(12) United States Patent
Schiavinato et al.

(10) Patent No.: US 7,863,256 B2
(45) Date of Patent: Jan. 4, 2011

(54) AMIDE DERIVATIVES OF HYALURONIC ACID IN OSTEOARTHROSIS

(75) Inventors: Antonella Schiavinato, Abano Terme-Padova (IT); Davide Bellini, Abano Terme-Padova (IT)

(73) Assignee: Fidia Farmaceutici S.p.A., Abano Terme-Padova (IT)

( * ) Notice: Subject to any disclaimer, the term of this patent is extended or adjusted under 35 U.S.C. 154(b) by 0 days.

(21) Appl. No.: 11/884,420

(22) PCT Filed: Feb. 20, 2006

(86) PCT No.: PCT/EP2006/001644

§ 371 (c)(1),
(2), (4) Date: Aug. 15, 2007

(87) PCT Pub. No.: WO2006/092233

PCT Pub. Date: Sep. 8, 2006

(65) Prior Publication Data

US 2008/0069884 A1 Mar. 20, 2008

(30) Foreign Application Priority Data

Mar. 2, 2005 (IT) .............................. PD05A0056

(51) Int. Cl.
*A61K 31/728* (2006.01)
*A61K 9/50* (2006.01)
*C08B 37/00* (2006.01)

(52) U.S. Cl. ........................... 514/54; 536/53; 424/488; 424/493

(58) Field of Classification Search ................. 424/488, 424/493; 514/54; 536/53
See application file for complete search history.

(56) References Cited

U.S. PATENT DOCUMENTS

| | | | |
|---|---|---|---|
| 5,612,360 | A | 3/1997 | Boyd et al. |
| 5,644,049 | A | 7/1997 | Giusti et al. |
| 5,657,582 | A | 8/1997 | Chitwood |
| 5,658,682 | A | 8/1997 | Dorigatti et al. |
| 5,733,891 | A | 3/1998 | Akima et al. |
| 6,110,967 | A | 8/2000 | Asao et al. |
| 6,579,978 | B1 | 6/2003 | Renier et al. |
| 6,831,172 | B1 | 12/2004 | Barbucci et al. |
| 2004/0014960 | A1 | 1/2004 | Moon et al. |

FOREIGN PATENT DOCUMENTS

| | | |
|---|---|---|
| EP | 0216453 A2 | 4/1987 |
| EP | 0 340 628 A2 | 11/1989 |
| EP | 0 416 250 A2 | 3/1991 |
| EP | 0 506 976 A1 | 10/1992 |
| EP | 0 554 898 A2 | 8/1993 |
| EP | 0 656 215 A1 | 6/1995 |
| EP | 0 713 859 A2 | 5/1996 |
| JP | 55161801 A | 12/1980 |
| JP | 3047801 A | 2/1991 |
| JP | 6-80666 A | 12/1993 |
| JP | 06-080666 A | 3/1994 |
| JP | 9188705 A | 7/1997 |
| JP | 9296005 A | 11/1997 |
| JP | 10120705 A | 5/1998 |
| JP | 10-298164 A | 11/1998 |
| WO | WO-89/02445 A1 | 3/1989 |
| WO | WO-92/06714 A1 | 4/1992 |
| WO | WO-92/20349 A1 | 11/1992 |
| WO | WO-95/24429 A1 | 9/1995 |
| WO | WO-96/35721 A1 | 11/1996 |
| WO | WO-98/47887 A1 | 10/1998 |
| WO | WO-98/54335 A1 | 12/1998 |
| WO | WO 00/01733 * | 1/2000 |
| WO | WO 0001733 A | 1/2000 |
| WO | WO-00/27887 A2 | 5/2000 |
| WO | WO 2004/011503 A | 2/2004 |

OTHER PUBLICATIONS

The Merck Manual, 1992, 16th Ed., pp. 1305-1307 and 1338-1341.*
MedicineNet, 2003, p. 1; 1998, p. 1 and 2005, p. 1.*
Moreland, R.W., Arthritis Res. Ther. 2003, 54-67.*
International Search Report, Jun. 22, 2006.
Aspinall et al., (Biochemistry (1994), 33(1), 250-5).
Danishefsky et al., Carbohydrate Research, vol. 16, pp. 199-205, (1971).
Japanese Office Action issued in Japanese application No. 2006-254511 on Feb. 2, 2010, which corresponds to co-pending U.S. Appl. No. 10/220,853.

(Continued)

*Primary Examiner*—Shaojia Anna Jiang
*Assistant Examiner*—Ganapathy Krishnan
(74) *Attorney, Agent, or Firm*—Birch, Stewart, Kolasch & Birch, LLP

(57) ABSTRACT

The present invention concerns amide derivatives of hyaluronic acid (HA) and biomaterials made of amide derivatives of hyaluronic acid (HA), particularly the hexadecylamide of HA, administered by the intra-articular route as a partial/total substitute for synovial fluid to treat joints affected by osteoarthrosis (OA) as well as cases of joint inflammation and/or trauma that cause damage to the cartilage and/or synovia (associated with pain).

Figure 1:
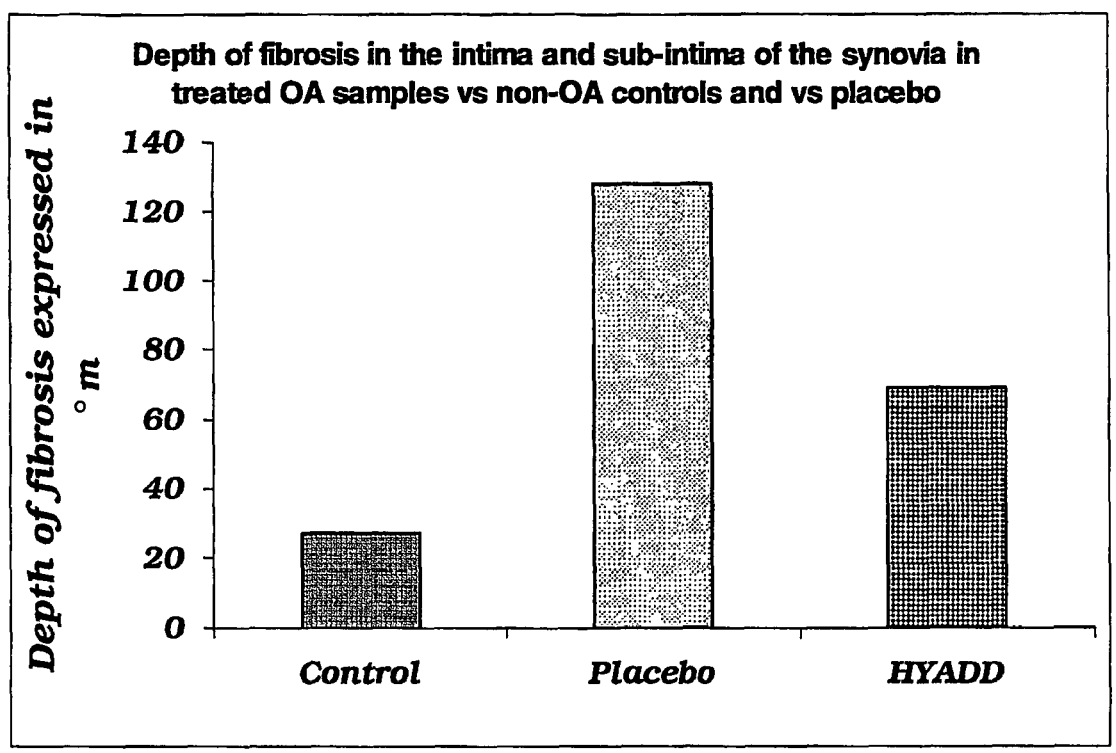

Lastly, we describe and claim their use in the treatment of joints where the entire structure shows signs of wear due to physiological aging.

32 Claims, 12 Drawing Sheets

OTHER PUBLICATIONS

Office Action issued in co-pending U.S. Appl. No. 10/220,853 on Nov. 18, 2003.
Office Action issued in co-pending U.S. Appl. No. 10/220,853 on Aug. 11, 2004.
Office Action issued in co-pending U.S. Appl. No. 10/220,853 on Mar. 29, 2005.
Office Action issued in co-pending U.S. Appl. No. 10/220,853 on Sep. 20, 2005.
Advisory Action issued in co-pending U.S. Appl. No. 10/220,853 on Jun. 26, 2006.
Office Action issued in co-pending U.S. Appl. No. 10/220,853 on Oct. 5, 2006.
Office Action issued in co-pending U.S. Appl. No. 10/220,853 on Aug. 27, 2007.
Advisory Action issued in co-pending U.S. Appl. No. 10/220,853 on Nov. 2, 2007.
Office Action issued in co-pending U.S. Appl. No. 10/220,853 on Jan. 17, 2008.
Office Action issued in co-pending U.S. Appl. No. 10/220,853 on Aug. 20, 2009.
Office Action issued in co-pending U.S. Appl. No. 10/220,853 on Mar. 8, 2010.
Search Report issued in CA application No. 2,339,066 on Oct. 5, 2004, which corresponds to co-pending U.S. Appl. No. 10/220,853.

* cited by examiner

AMIDE DERIVATIVES OF HYALURONIC ACID IN OSTEOARTHROSIS

SUBJECT OF THE INVENTION

The present invention concerns a biomaterial made of amide derivatives of hyaluronic acid (HA), particularly the hexadecylamide of HA, administered by the intra-articular route as a partial/total substitute for synovial fluid to treat joints affected by osteoarthrosis (OA) as well as cases of joint inflammation and/or trauma that cause damage to the cartilage and/or synovia (associated with pain). Lastly, we describe and claim their use in the treatment of joints where the entire structure shows signs of wear due to physiological aging.

BACKGROUND OF THE INVENTION

Osteoarthosis/osteoarthritis (OA) is a seriously disabling condition characterised by a progressive erosion of joint cartilage due to degradation of the joint matrix and loss of the main cell components: chondrocytes.

The exact etiology of the condition is still unclear. However, recent studies have shown it may be triggered by mechanical imbalance affecting the whole joint. Mechanical joint instability may be caused by various factors (e.g. trauma and/or mechanical stress involving the joint capsule in toto, inflammation of the joint system) and may upset the delicate balance between synthesis and degradation of the extracellular matrix, which is mainly synthesised by chondrocytes and synoviocytes.

When this perfect, but fragile, homeostasis is upset, degradation of the matrix is uncompensated by its synthesis because of the loss of chondrocytes, and gradually worsens.

Indeed, excessive and/or incorrect loading of the joint may cause a chondrocyte response that manifests itself in synthesis of the very enzymes responsible for degradation of the cartilage, protease enzymes called metallo-proteinase (MMP). These are synthesised by the chondrocytes when stimulated by inflammatory cytokines, such as IL-1 and TNF-α, that are produced and released in the joint cavity, particularly at the onset of an inflammatory pathology. IL-1 also stimulates synthesis of high levels of nitric oxide (responsible for chondrocyte death by apoptosis) as well as inhibiting proteoglycan synthesis (matrix components) by the chondrocytes themselves (Dozin B. et al., Matrix Biology, 2002, 21:449-459).

It is known that the extracellular matrix must be integral for chondrocytes to survive. Data in the scientific literature have demonstrated that degradation of molecules from the matrix may lead to the release of other molecules (that likewise derive from degradation of the matrix) similarly capable of inducing chondrocyte apoptosis (Cao L. et al., Exp Cell Res, 1999, 246:527-537).

For this reason, the cartilage of osteoarthrotic patients presents a decrease in cellularity and corresponding increase in the formation of empty "lacunae" within the joint matrix.

High levels of IL-1 have been found in the synovial fluid of patients suffering from rheumatoid arthritis (RA) and psoriatic arthritis (Arend W. P. et al., Arthritis Rheum, 1995, 38:151-160).

The physiological aging process of the joint surfaces also seems to involve the enzymatic mechanisms peculiar to OA. Consequently, the therapies normally used to treat this pathology are also applied to joints with cartilage partially or totally damaged by "normal" joint aging.

The cartilage matrix is constituted by a three-dimensional structure formed by molecules of collagen and aggregated proteoglycan complexes. These in turn are constituted by a supporting structure based on hyaluronic acid that interacts with glycosaminoglycan molecules (GAG), non-covalently bound to polypeptide sequences associated with hyaluronic acid (HA), thus giving the cartilage both mechanical and viscoelastic properties.

Indeed, HA is a molecule with special viscoelastic properties, synthesised and secreted also in the joint cavity mainly by the synoviocytes (Asari A. et al., Arch Histol Cytol, 1995, 58(1):65-76) and it is therefore one of the main components of synovial fluid. When the joint is moved slowly, HA acts as a viscous lubricant, while when it is moved briskly HA's elastic properties enable it to act as a shock absorber counteracting any trauma or microtrauma to which the joint may be exposed.

It is known that the functional characteristics of the synovial fluid depend on both the concentration and degree of polymerisation of HA, and that any changes in these may lead to OA-type histological damage to the joint.

The turnover of HA (and of glycosaminoglycans in general) in healthy synovial fluid is usually rapid (1 day in the sheep), but in the course of OA, a drop in its concentration (associated with a decrease in GAG) and its mean molecular weight (MW) has been observed, as well as a marked decrease in its turnover (Balazs E A. et al., J Rheumatol Suppl, 1993, 12:75-82; Belcher C. et al., Annals of the Rheumathic Disease, 1997, 56:299-307).

Further findings have shown that HA not only has biomechanical viscosupplementation properties, but also the ability to protect chondrocytes from the action of IL-1, measured as the percentage of proteoglycan synthesis (Brun P. et al., OsteoArthritis and Cartilage, 2003, 11:208-216), (Stove J. et al., Journal of Orthopaedic Research, 2002, 20:551-555).

Based on these observations, it was Balazs who first suggested that the evolution of osteoarthrosis might be modified by administering exogenous HA, especially high-molecular-weight HA, directly into the joint cavity.

There are various drugs currently on the market for the intra-articular administration of HA in OA, such as: Hyalgan®, HA purified from rooster combs with a MW of: 5-7.5× $10^5$ Da (European patent No. 0138572 B1); Synvisc®, (Hylan G-F 20) HA cross-linked with formaldehyde and divinyl sulphone with a MW of: 6-7×$10^6$ Da (U.S. Pat. No. 4,713,448), Artz®, HA with MW: 6.2-12×$10^5$ Da.

Moreover, European patent No. 1144459 B1 describes and claims a new HA derivative for the treatment of OA joint pathologies. It is a hyaluronic acid derivative cross-linked with polyamines to form amide bonds with the carboxy groups of HA. It is in the form of a generally water insoluble hydrogel, prepared and subsequently tested with a final degree of cross-linking of 50% (Barbucci R. et al., Biomaterials, 2002, 23:4503-4513).

Intra-articular injections of HA are known to provide viscosupplementation and improve function in limbs affected by OA pathology, with a consequent reduction in joint pain. However, HA's residence time in the joint capsule is limited to about 40 hours after application of Hyalgan® (Fraser J R. et al., Seminars in Arthritis and Rheumatism, 1993, 22:9-17) while in the case of Synvisc® it may last for a few days (Fiorentini R., Proceedings of the US FDA Advisory Panel on Orthopaedic and Rehabilitation Devices, Nov. 21, 1996 Fairfax (VA):CASET Associates, 1996; Berkowitz D., Proceedings of the US FDA Advisory Panel on Orthopaedic and Rehabilitation Devices, Nov. 20, 1996 Fairfax (VA):CASET Associates, 1996).

This limitation means that weekly administration cycles are usually called for, with a total of at least 5 intra-articular injections.

Moreover, some of these drugs based on chemically modified HA, such as Synvisc®, have been involved in reports of sometimes serious adverse events (Hammesfahr J F. et al., The American Journal of Orthopaedics, 2003, 32:277-283), probably following the onset of inflammatory processes, especially linked with eosinophil recruitment (Schiavinato A. et al., Clinical and Experimental Rheumatology, 2002, 20:445-454).

Considering the above, new chemical derivatives of HA are being studied that enable the problems linked with both residence time in the joint cavity and the risk of toxicity due to solvents and/or particular chemical agents used in the chemical modification of HA to be overcome, while maintaining all the characteristics and intrinsic properties of the polysaccharide unaltered.

The Applicant has surprisingly discovered that HA, chemically bound to an amine by its carboxy group and called HYADD™ (European patent No. 1095064 B1), has all the intrinsic properties of HA described above, demonstrating, moreover, that it provides a surprising proliferative stimulus towards OA human chondrocytes, elicits a protective action on OA synovia, slowing down the degenerative process, reducing the changes in the morphology of OA cartilage surface and the formation of osteophytes (the bony formations typical of osteoarthrosis), thus representing a new curative therapy for OA and, lastly, that it possesses viscoelastic characteristics that allow the partial and/or complete integration/substitution of the synovial fluid in a joint that has been damaged or treated by surgery, enabling correct, painless loading of the knee.

BRIEF DESCRIPTIONS OF THE DRAWINGS

FIG. 1: Graph depicting the Depth of fibrosis in the intima and sub-intima of the synovia in treated OA samples vs non-OA controls and vs placebo.

Figure 2:
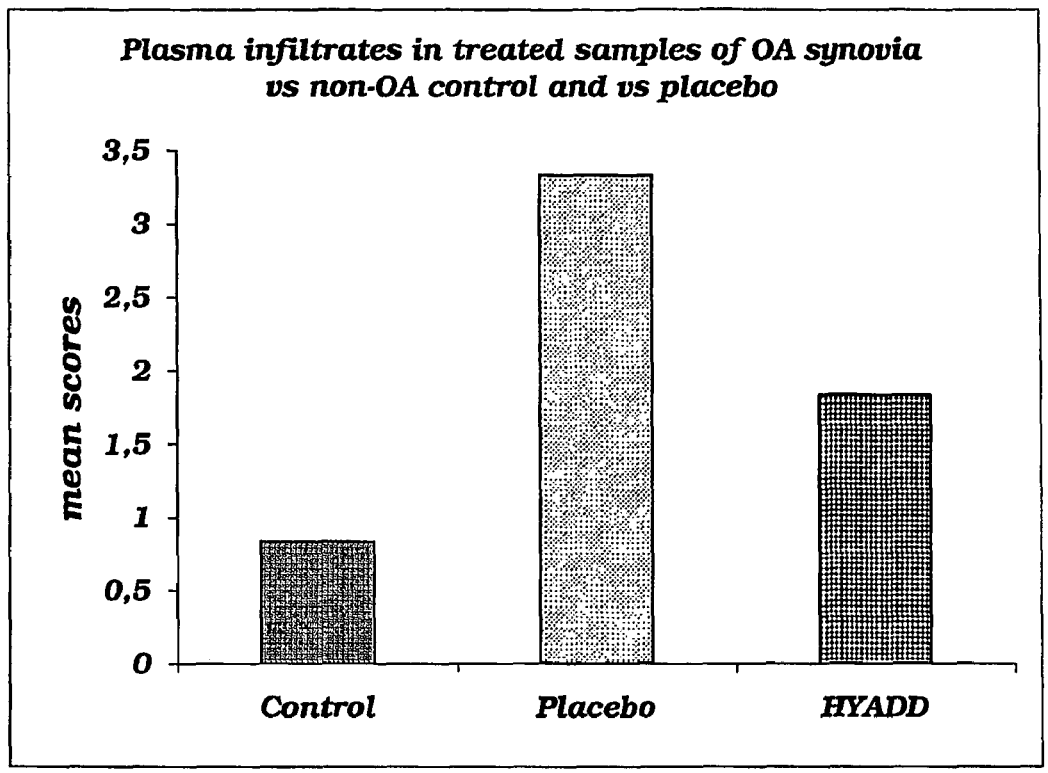

FIG. 2: Graph depicting the Plasma infiltrates in treated samples of OA synovia vs non-OA control and vs placebo.

Figure 3:
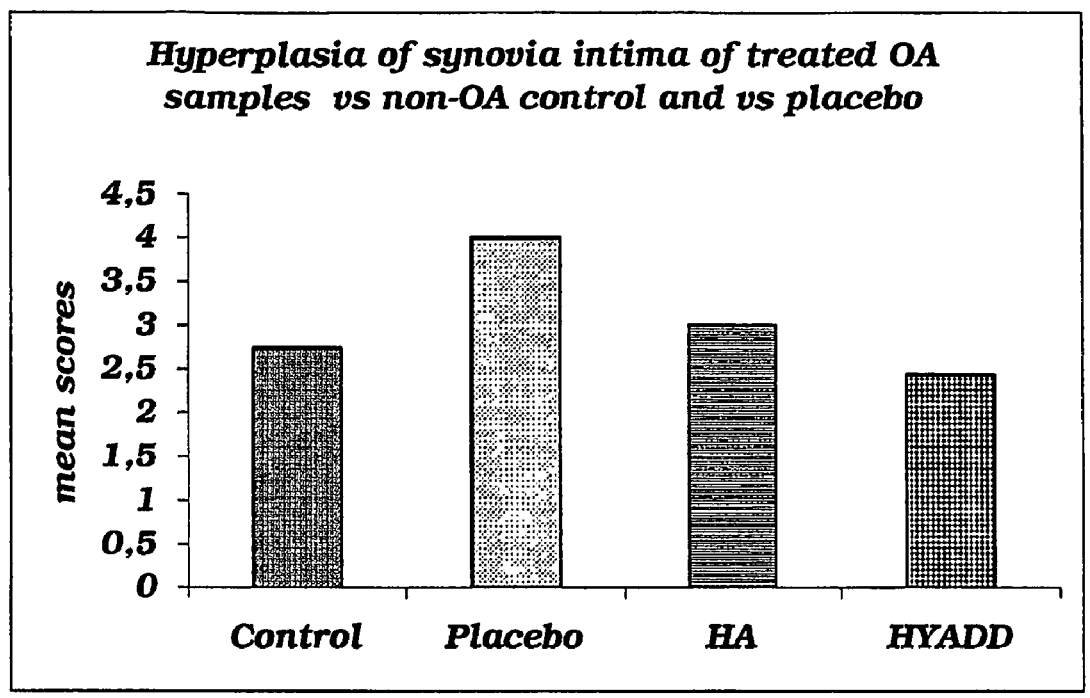

FIG. 3: Graph depicting the Hyperplasia of synovia intima of treated OA samples vs non-OA control and vs placebo.

Figure 4:
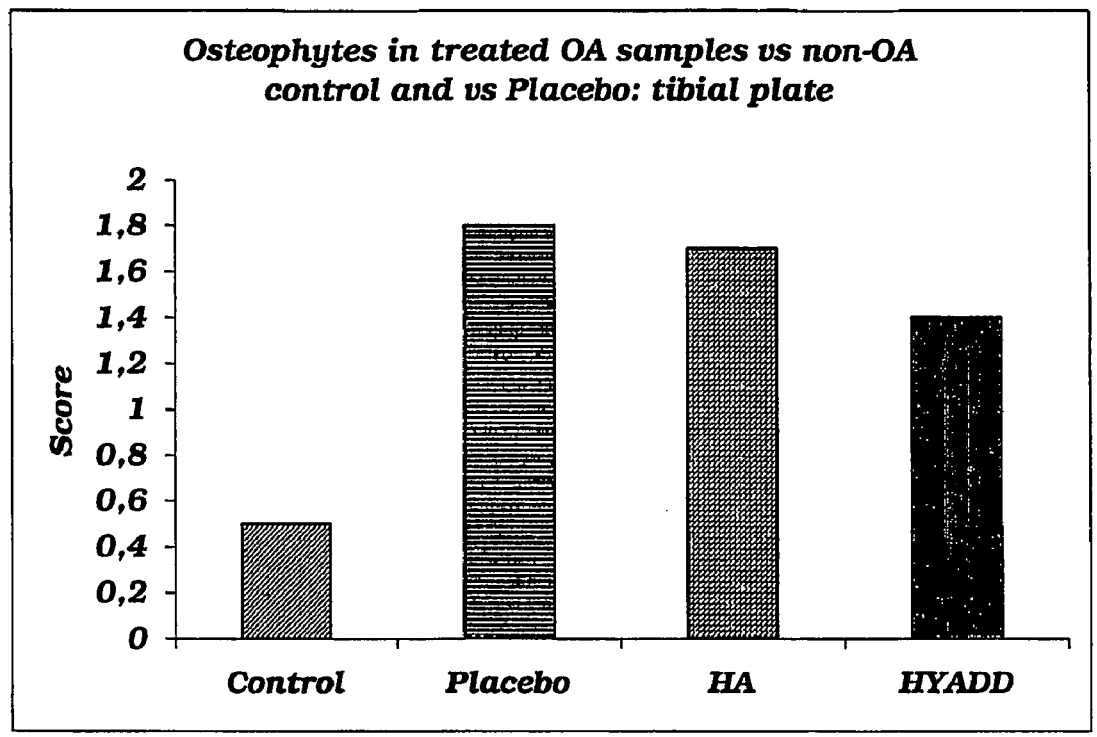

FIG. 4: Graph depicting the Osteophytes in treated OA samples vs non-OA control and vs Placebo: tibial plate FIG. 5: Graph depicting the Osteophytes in treated OA samples vs non-OA control and vs placebo: femoral condyle FIG. 6: Graph depicting the Assessment of samples of treated OA cartilage vs non-OA control and vs placebo: femoral condyle FIG. 7: Graph depicting the Assessment of samples of treated OA cartilage vs non-OA control and vs placebo: tibial plate FIG. 8: Graph depicting the Concentration of glycosaminoglycans in the synovial fluid of treated OA samples vs placebo FIG. 9: Graph depicting the Viscosity of the synovial fluid of treated OA samples vs placebo FIG. 10: Graph depicting the Residence time of HYADD in the joint cavity FIG. 11: Graph depicting the Concentration of $^3$H-labelled HA synthesized by treated OA synoviocytes vs Placebo FIG. 12: Graph depicting the Proliferation of arthrotic human chondrocytes treated with HYADD 0.5-1.5 mg/ml

DETAILED DESCRIPTION OF THE INVENTION

European patent No. 1095064 B1 describes and claims amide derivatives of HA that originate from the formation of an amide bond between the carboxy group of HA and the amine group of an amine belonging to the aliphatic, aromatic, arylaliphatic, cycloaliphatic, heteroaliphatic series. The compounds that derive therefrom (called HYADD™) can present different degrees of amidation, ranging from 0.1 to 5%, (Example 1) so that the final product is soluble in water, phosphate buffer or saline solution.

Said derivatives have been described with regard to the preparation of pharmaceutical compositions formulated in various different ways, in the preparation of biomaterials made into different forms for the preparation of surgical articles and, lastly, in forms suitable for the coating of biomedical objects such as catheters and stents.

Their use has also been claimed in a vast range of clinical practices, including orthopaedics. However, their use has never been described, claimed, or even hypothesised, as a biomaterial to be used specifically at an intra-articular level as a curative therapy for OA, or for RA and psoriatic arthritis, in all cases of inflammation and/or joint trauma causing damage to the cartilage and/or synovia (associated with pain) and lastly, as a therapy for pathologies associated with aging of the joint.

In particular, it is object of the present invention the use of amide derivatives of hyaluronic acid for the preparation of a medicament for the treatment of osteoarthrosis/osteoarthritis.

Amide derivatives of hyaluronic acid as partial and/or total substitutes for the synovial fluid in the treatment of joints affected by osteoartrosis, trauma, inflammation and/or wear due to aging of the joint structure are also object of the present invention. Biomaterials constituted by the amide derivatives of hyaluronic acid are also object of the present invention.

By the experiments described hereafter, the Applicant has demonstrated that:
HYADD™ derivatives possess the intrinsic properties of HA, with a decidedly longer residence time in the joint than that of native HA;
they exercise a strong proliferative stimulus on OA chondrocytes and therefore promise to be an effective new therapy for the cure of damaged cartilage;
they exercise an unexpected protective action on OA synovia and cartilage, slowing down the degenerative process;
they have viscoelastic properties that enable the partial and/or complete integration/substitution of the synovial fluid in a joint which is damaged/inflamed/aged or which has undergone surgery;
they have no toxic effect on chondrocytes or synoviocytes treated in vitro and in vivo;
lastly, for all the above reasons, the HYADD™ derivatives have proved active in reducing OA-associated pain, thus enabling correct loading of the joint.

Based on the above, the Applicant claims HYADD™ derivatives as biomaterials to be used to substitute partially/totally the synovial fluid in the treatment of joints, especially those affected by OA and, moreover, for joints affected by trauma and/or inflammation, or that have been damaged by the physiological aging process or treated by surgery.

The HA derivatives known as HYADD™ described in the present invention are synthesised according to European patent No. 1095064 B1, starting with an HA derivative from any source, for example, obtained by extraction from rooster combs (European patent No. 0138572 B1), or by fermentation or by technological means, and have a molecular weight ranging between 400 and 3×10⁶ Da, in particular between 1×10⁵ Da and 1×10⁶ Da, and even more particularly between 500,000 and 750,000 Da.

The HYADD™ derivative used in all the experiments performed, both in vitro and in vivo, has an average degree of amidation of 2-3%, and was synthesised using hexadecylamine with carbonyl diimidazole as the preferred activating agent (Example 2).

The product obtained is water soluble and can be sterilised by the methods known to experts in the field. However, sterilisation by autoclave is preferable.

In particular, in the amide derivatives of hyaluronic acid according to the present invention the amide is formed by amide bond between the carboxy group of hyaluronic acid and the amine group of an amine belonging to the aliphatic, aromatic, arylaliphatic, cycloaliphatic or heteroaliphatic series. The amine is preferably hexadecylamine. The degree of amidation ranges between 0.1 and 5%. More preferably the mean degree of amidation is 2% or 5%.

The amide derivatives of hyaluronic acid according to the present invention are made in the form of gels, hydrogels, powders, microspheres, nanospheres.

The purpose of the experiments described hereafter was to analyse both the viscosity and chemical/biological properties of the HYADD™ derivative:
  in vivo for histological analysis of the synovia (synovial membrane) in OA sheep after intra-articular treatment (described in detail hereafter).
  in vivo to analyse the morphology of OA cartilage surface and assess the presence of osteophytes after intra-articular treatment (described in detail hereafter);
  in vivo to measure the concentration of glycosaminoglycans present in the synovial fluid of OA sheep before and after intra-articular treatment (described in detail hereafter);
  in vivo to determine the intrinsic viscosity of the synovial fluid of OA sheep joints before and after intra-articular treatment (described in detail hereafter);
  in vivo to assess the residence time in the joint cavity and location in the joint cartilage;
  in vitro using cultures of synoviocytes taken from OA joints of sheep that had received intra-articular treatment (described in detail hereafter) to assess HA's capacity for synthesis;
  in vitro using cultures of human OA chondrocytes to verify their proliferative effect and toxicity.

Materials, Methods, and the Results Obtained from the Experiment In Vivo: Model of OA in Sheep Joints 18 Merino sheep aged 7-8 years first underwent meniscectomy for removal of the lateral part of the meniscus in both front limbs; 16 weeks after surgery, OA was evident, as described in Ghosh P. et al., Proceeding Hyaluronan 2003 Congress, Ed. Matrix Biology Institute 2004 e in Little C. et al., J Rheumatol, 1997, 24:2199-2209.

Treatment

The 18 animals were then divided into 3 groups, each given a different treatment starting the 16$^{th}$ week after surgery and ending in the 20$^{th}$ week:
  OA+Placebo: the animals were treated weekly with 1 intra-articular injection of 2 ml of sterile saline solution, for a total of 5 injections;
  OA+HA: the animals were treated weekly with 1 intra-articular injection of 2 ml of HA (MW 500,000-730,000 D), for a total of 5 injections;
  OA+HYADD™: these animals were treated every two weeks with 1 intra-articular injection of 2 ml of HYADD™ (Hexadecylamide of hyaluronic acid with a MW of PM 500,000-730,000 D and a mean degree of amidation of 2%) diluted in phosphate buffer solution (PBS) at a final concentration of 5 mg/ml, for a total of 3 injections.

The animals were sacrificed in the 26$^{th}$ week.

Synovial fluid was taken from the sheep immediately before the start of treatment and 1 week before sacrifice (hence, 5 weeks after the end of treatment), while the synovia and cartilage were removed at the time of sacrifice.

Analyses Performed In Vivo:

Histology of the Synovia

The samples of synovia from the joints subjected to meniscectomy and treated as described above, were first immersed in buffered formalin solution (10% in PBS) for 24-48 hours. After dehydration with alcohol and xylol, they were embedded in paraffin and processed as known to an expert in the field to obtain sections 4 µm thick, subsequently stained with haematoxylin and eosin. To the 3 groups of samples treated as described, a 4th group of non-operated animals was added, representing "non-OA controls".

The synovial membrane covers the entire inside non-cartilage surface of the joint cavity and is constituted by connective tissue. Structurally, it is composed of three layers, known as the intima, subintima and subsynovial. In the intima, regularly arranged reticular and collagen fibres can be seen, that increase in number in the subintima and subsynovial. Said sections were analysed under an optical microscope using a grid of 1 cm² which, with a 40× magnifying lens, projected a visual field of 250 µm of each area analysed. Five randomly selected areas were analysed per section. The parameters considered (chosen because they characterise OA), were the following: hyperplasia of the intima, presence of plasma infiltrations in the intima and fibrosis of the synovial membrane (manifested by an "untidy" arrangement of the collagen fibres in the synovia).

Fibrosis of the synovia was assessed by measuring the depth of the subintima up to a maximum value of 250 µm. Scoring in the first two parameters was based on the table below:

| Parameters | Score | Observations |
|---|---|---|
| Hyperplasia of the intima | 0 | Presence of 1-2 layers of cells; |
| | 1 | Between 3 and 4 layers; |
| | 2 | 5 o layers or more; |
| | 3 | 5 layers or more all along the intima. |
| Plasma infiltrations | 0 | None; |
| | 1 | 1 focus of infiltration; |
| | 2 | between 2 and 5 foci; |
| | 3 | Presence of 5 or more scattered foci. |

Results:

Meniscectomy caused a significant increase in all the histological parameters analysed, compared to the non-operated controls (which represent an OA-free situation), thus demonstrating the validity of the model of OA induction that was used. In all cases, treatment with HYADD™ (FIGS. 1, 2 and 3) determined a marked and significant improvement in the parameters considered, with regard to treatment with both Placebo and HA (FIG. 3) and, in one case (FIG. 3), HYADD™ even gave the same result as the non-OA control.

Joint Cartilage Analysis

In parallel with the histological analysis of the synovial membrane, macroscopic morphological analysis was performed on the joint cartilage of the OA animals compared to the non-treated ones (placebo) and the controls (in this case too, a fourth group of non-operated animals representing "non-OA controls" was added to the three groups). The joints were opened to analyse the surface of the medial joints connecting the tibia and femur. Assessments were based on the Gross Morphology Score System of Cake et al., Osteoarthritis and Cartilage, 2000, 8:404-411, used to assess both cartilage damage and the effects of treatment.

The Score System estimates both the integrity of the cartilage and the development of osteophytes (bony formations typical of osteoarthrosis) by applying the following scores:

| Parameters | Score | Observations |
| --- | --- | --- |
| Cartilage integrity | 0 | Normal; |
|  | 1 | Roughening; |
|  | 2 | Fibrillation and fissures; |
|  | 3 | Small erosions (<5 mm) |
|  | 4 | Larger erosions (>5 mm) |
| Osteophyte (os.) development | 0 | Normal; |
|  | 1 | Slight os. development; |
|  | 2 | Moderate os. development; |
|  | 3 | Large os. development; |

Figure 5:
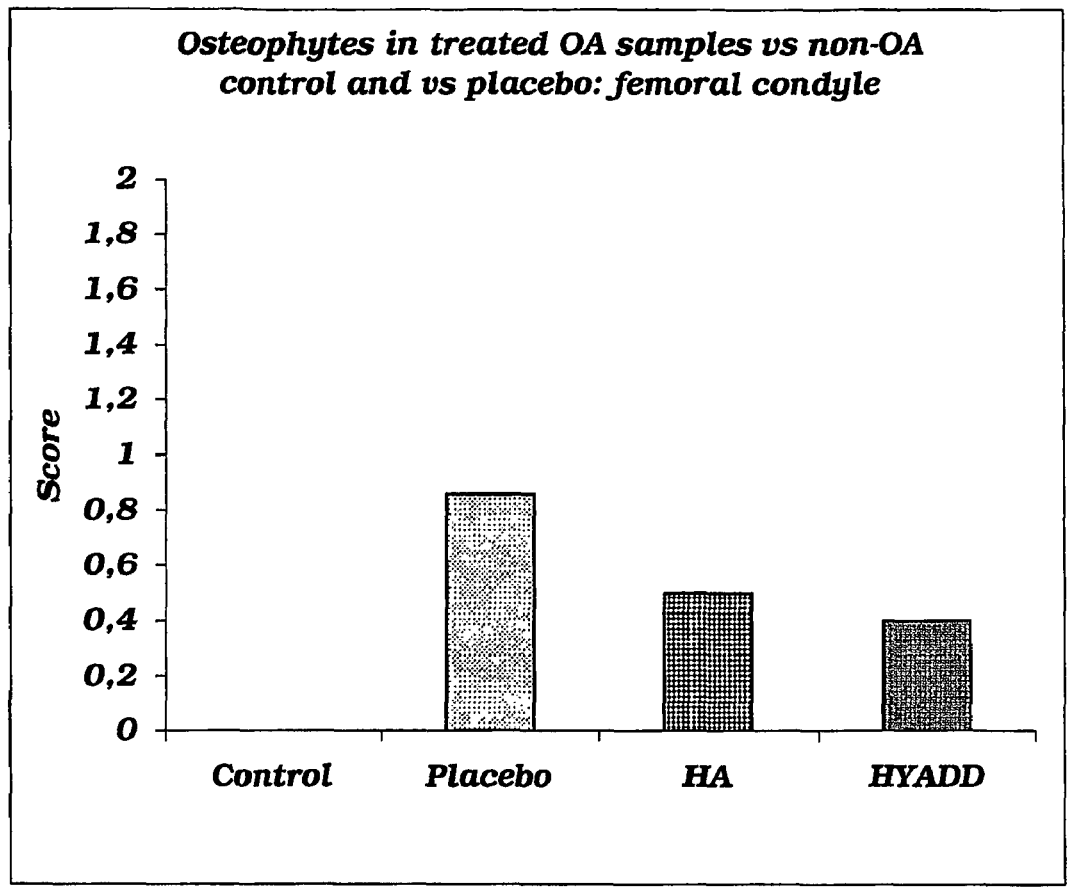

Results:

The animals treated with placebo had the highest scores for osteophyte development (FIGS. 4-5). Treatment with HYADD® significantly reduced the development of such alterations, particularly evident in the medial compartment of the femoral condyle (FIG. 5).

Figure 6:
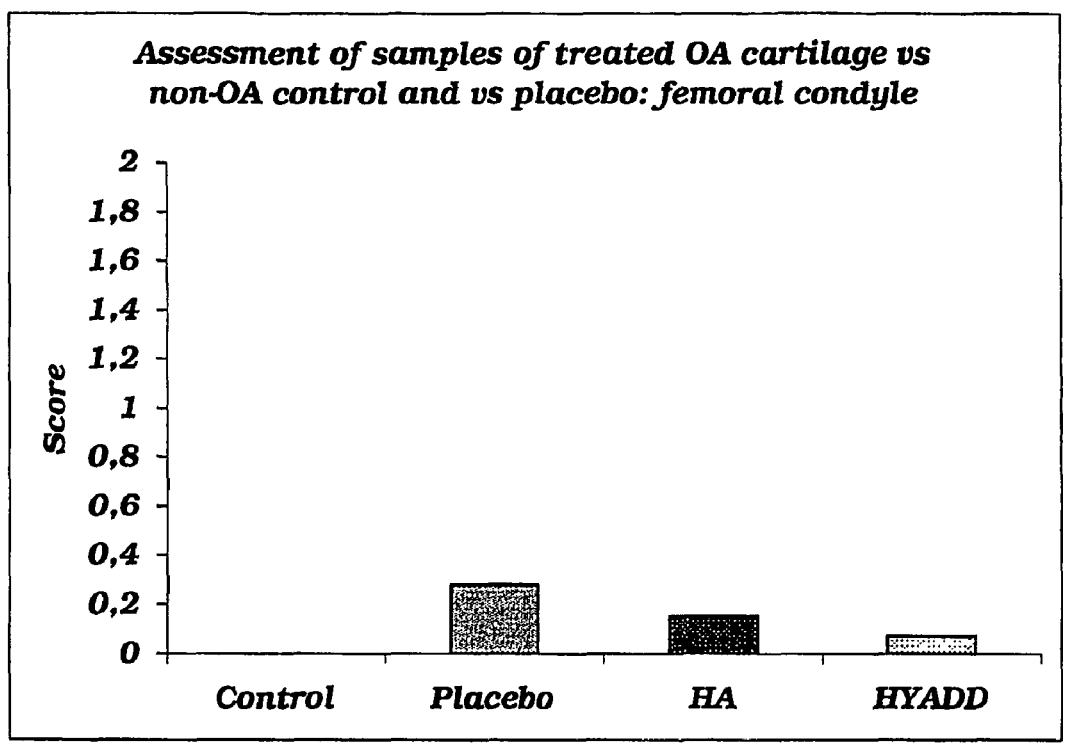
Figure 7:
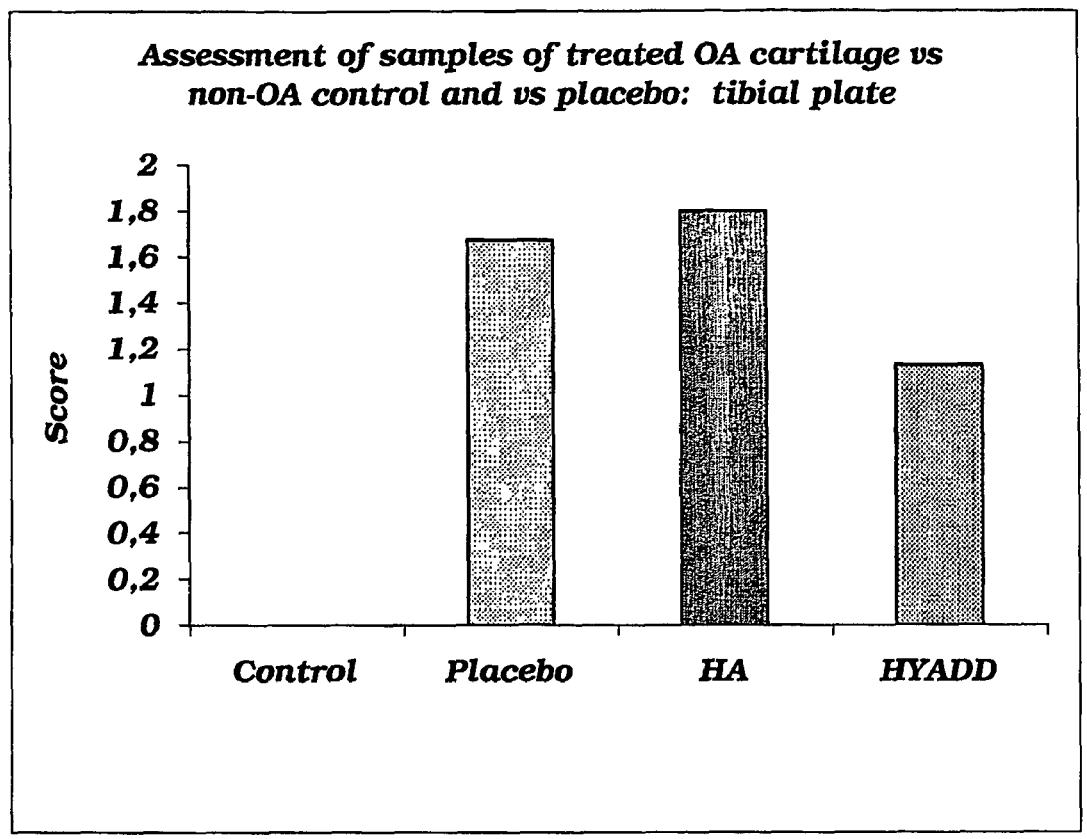

Similarly, the highest scores relative to cartilage damage were seen in the animals treated with placebo, while the cartilage of the group treated with HYADD® was the least altered, considering both the tibial plate and the femoral condyle (FIGS. 6-7).

Glycosaminoglycan Concentration

The purpose of this analysis was to assess and compare the concentration of sulphated glycosaminoglycans (GAGs) present and/or newly synthesised in the synovial fluid of the treated animals vs placebo. The analysis was performed using the technique described by Farndale R W. et al., Connective Tissue Res., 1982, 9:247-248, and perfected by Appleyard R C. et al., Osteoarthritis Cartilage, 2003, 11:65-77.

Figure 8:
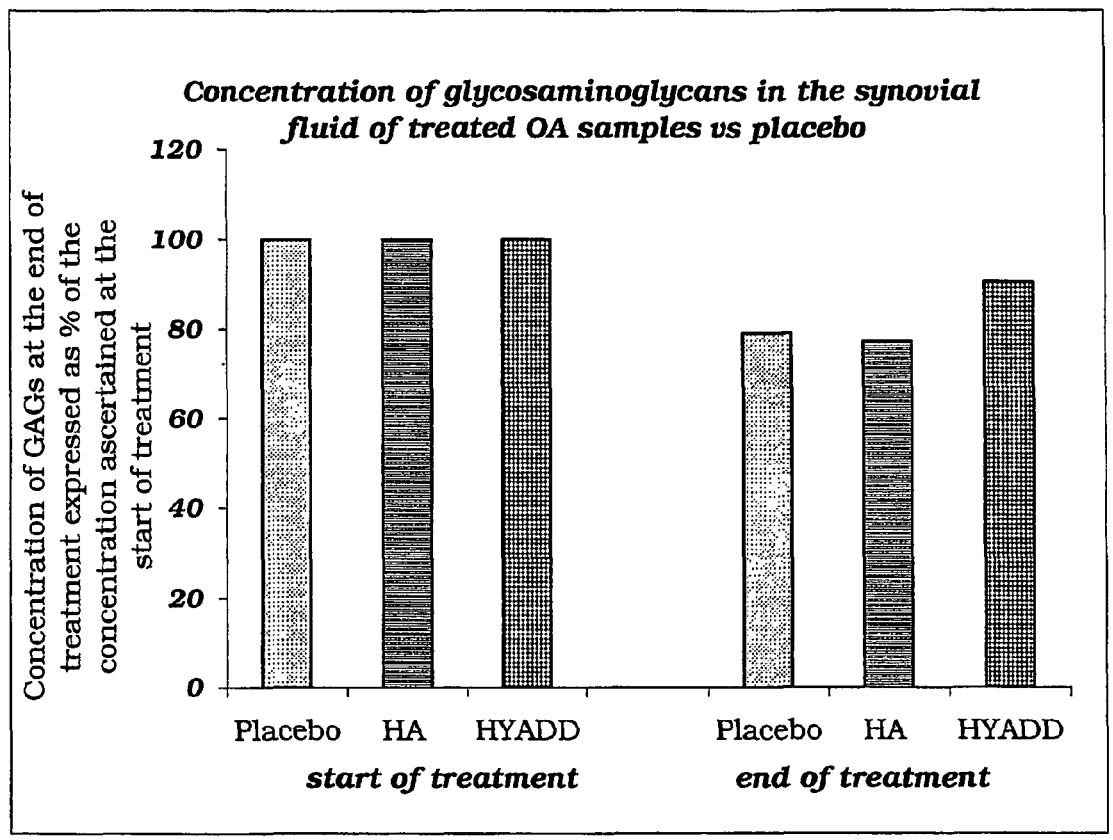

The results are shown as a graph in FIG. 8 as the concentration of GAGs determined at the end of treatment and expressed as a percentage of the concentration measured at the start of treatment. FIG. 8 shows that treatment with HYADD™ alone determines a greater increase than placebo in the concentration of GAGS in the synovial fluid at the end of the experiment (which, conversely, gives substantially lower values than at the start of treatment, as discussed previously), GAGs which might derive from greater synthesis by the synoviocytes of synovial tissue stimulated and protected by the HA amide in question.

Dynamic Viscosity

The dynamic viscosity of the synovial fluid (i.e. its intrinsic viscosity) was measured at the beginning and 5 weeks after the end of each treatment with a Micro Fourier Rheometer. All the findings were calculated and compared with one another at a frequency of 0.5 Hz (Ghosh P. et al., Proceedings Hyaluronan 2003 Congress, Ed. Matrix Biology Institute 2004).

Figure 9:
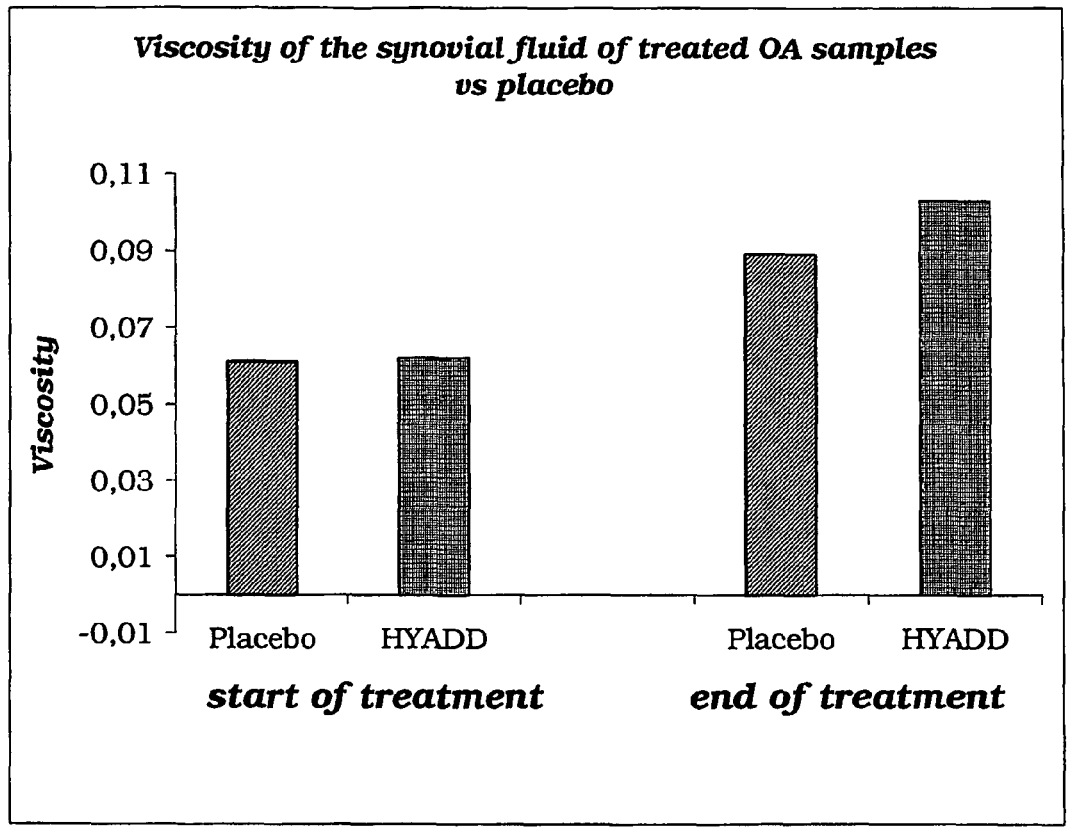

The results are shown in FIG. 9: HYADD™ treatment determines a significant increase in intrinsic viscosity in the treated animals, compared to placebo.

Residence Time

The residence time of HYADD™ in the joint cavity was assessed in non-OA rabbit joints: 5 groups of 5 rabbits each were given a single intra-articular injection of 0.25 ml of HYADD™ at an initial concentration of 5 mg/ml (each joint therefore received 1.25 mg of HYADD™), and analysed 15, 25, 35, 45 and 55 days after administration.

Residence time in the joint was determined by HPLC analysis of the amine residue (of the HYADD™ derivative) present in the synovial fluid taken from the treated joints, at the set times, after euthanasia of the animals.

The synovial fluid samples were treated with NaOH before hydrolysis at 70° C., thus enabling complete release of the hexadecyl amine from the molecule in question. The amine was then extracted from the solution with diethylether, dissolved in methanol and prepared for chromatographic analysis by the HPLC technique with fluorometer (excitation wavelength 330 nm, emission wavelength 440 nm).

By quantifying the hexadecyl amine in the samples, it is possible to establish the concentration of HYADD™ in the synovial fluid.

Figure 10:
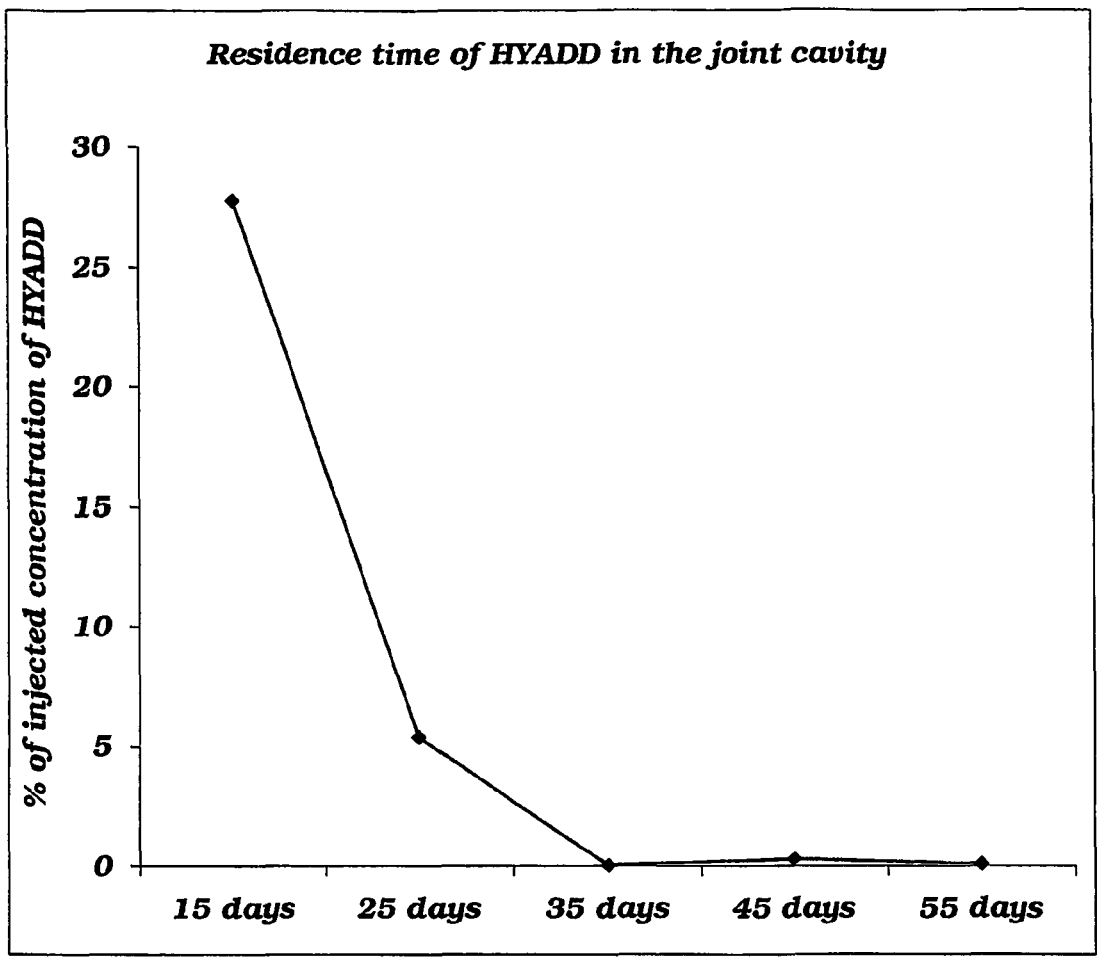

The resulting residence time was 15 days, because 27% of the initial derivative was still present in the joint cavity after this time, but this value had dropped to 5% 25 days after injection, as shown in FIG. 10.

Determining the Location of Preference of the HYADD™ Derivative

For this type of experiment, we used the HYADD™ derivative labelled with the isotope $^{14}C$: ($^{14}C$)-HYADD™ with specific initial activity of 3.01 $\mu CI.mg^{-1}$, prepared and supplied by ABC Laboratories. The derivative ($^{14}C$)-HYADD™ was prepared in phosphate buffer at an initial concentration of 8 $mg.ml^{-1}$; 0.4 ml of the resulting solution was injected into the joint cavities of 5+5 rabbits which were later sacrificed on the $2^{nd}$ and $14^{th}$ days after treatment when the radioactivity present on the cartilage surface was analysed. The samples of cartilage taken were first exposed to basic hydrolysis with NaOH 2M for 30 minutes at 70° C. Each sample was then washed with buffer and the washing buffer pooled with the previous solutions of NaOH. The samples were then mixed with Quickszint 1 scintillation fluid (in a ratio of 1:10) for the final radioactivity reading, then the radioactivity was determined using a Packard TR 2100 scintillation analyser.

The results obtained were expressed as the percentage of initial injected radioactivity. Two days after the intra-articular injections, the % of radioactivity recovered after basic hydrolysis of the cartilage was 2% of that initially injected, while the value dropped to 1% 14 days after treatment.

This result clearly indicates that the HYADD™ derivative does not remain confined to the synovial fluid after being injected intra-articularly, but can be found on the surface of the joint cartilage as early as two days later, thus confirming that the amide derivative, subject of the present invention, represents a new therapy for the treatment of OA.

In Vitro Analyses:

OA Sheep Synoviocytes in Culture

Materials, Methods and Results Obtained from the Experiment

Cells:

The synovial membranes used in the following experiment was taken from the animals treated with HYADD™ and HA and from the respective controls, as previously described for the in vivo experiment.

They were first chopped in a Petri dish, washed and centrifuged with phosphate buffer solution (PBS) at 2000 rpm at 20° C. for 10 minutes, then resuspended in PBS containing trypsin (0.2%) and EDTA (0.1%). The digested material was washed and centrifuged with culture medium (DMEM) and then resuspended in DMEM containing foetal calf serum FCS (10%). The cells thus obtained were recentrifuged at 2000 rpm for 10 minutes and the pellet was collected with culture medium (DMEM/FCS) containing 2 mg/ml of collagenase. After 3 hours' incubation at 37° C., the cells were centrifuged and seeded in Petri dishes with DMEM containing 10% FCS. The cells thus obtained were expanded to the second passage. The medium was renewed every 2/3 days and, when the cells had reached 90% confluence, used to determine HA synthesis, by incubating the synoviocytes with set aliquots of $^3$H-acetate (Amersham Pharmacia Boitech). The cells were then treated as described by Ghosh P. et al., Proceedings Hyaluronan 2003 Congress, Ed. Matrix Biology Institute 2004 for the final determination of the $^3$H-acetate incorporated in the HA molecules synthesised in vitro by the synoviocytes.

Figure 11:
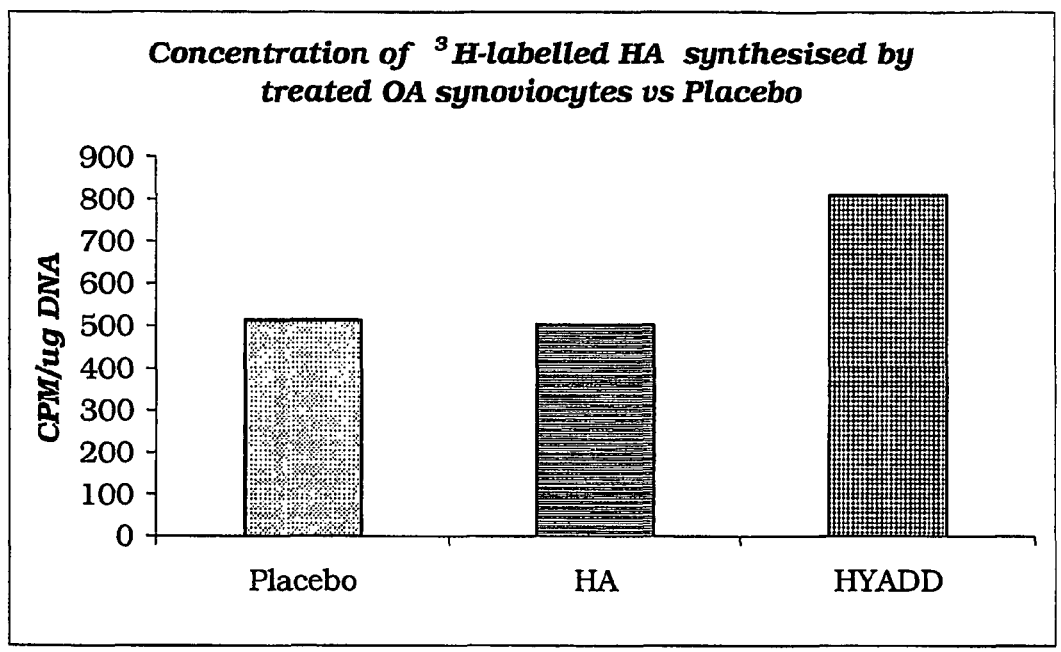
Figure 12:
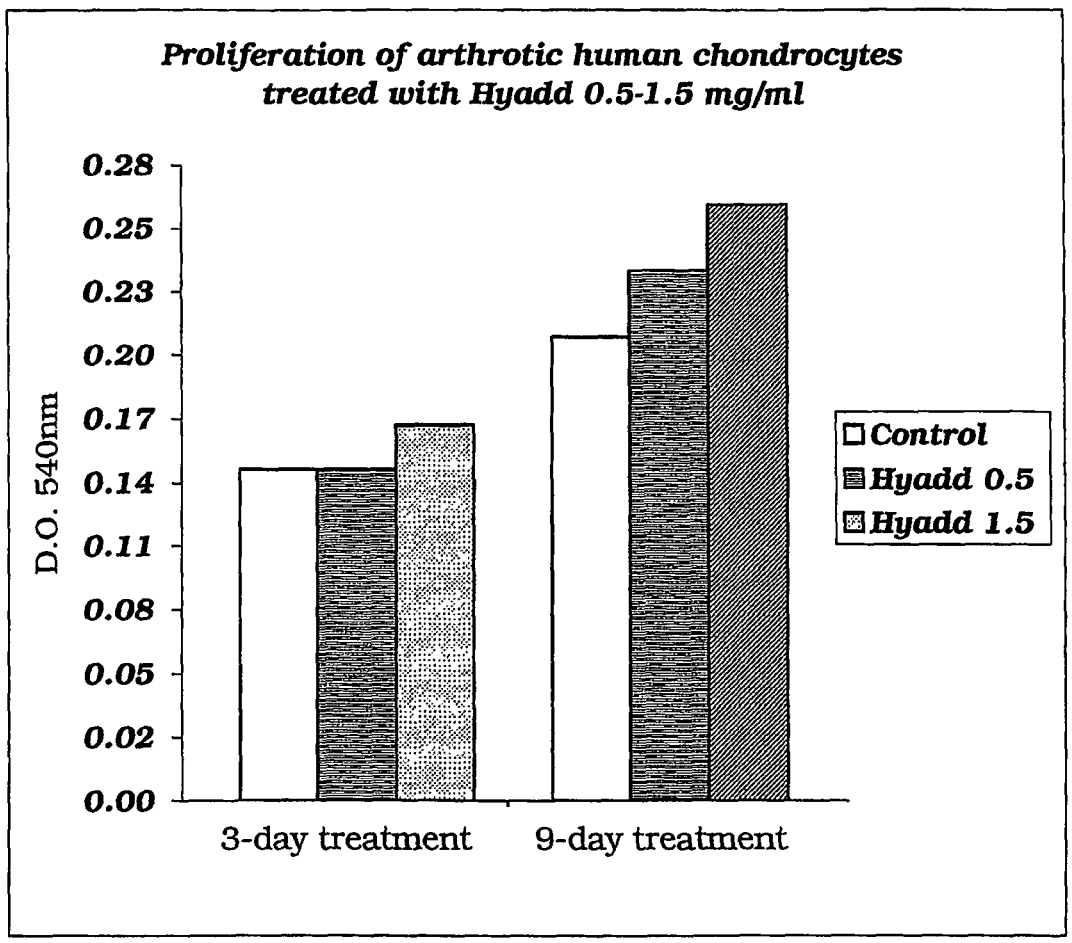

Results:

The results obtained show that treating OA joints with HYADD™ protects the synoviocytes from the cytotoxic action of the proinflammatory cytokines normally present in OA joints, favouring/maintaining unaltered their cell metabolism, demonstrated by their high capacity for HA synthesis, as shown by the experimental data in FIG. 11, obtained with synoviocytes taken from OA sheep treated HYADD™ vs placebo.

Human OA Chondrocyte Cultures

Materials:

HYADD™ (hexadecylamide of hyaluronic acid with a MW of 500,000-730,000 D and a mean degree of amidation of 2%) diluted in phosphate buffer to a final concentration of 3 mg/ml.

Cells:

Human chondrocytes: the cells were obtained by biopsy from joint cartilage from patients who had undergone surgery for joint replacements. In short, the samples were minced and treated with trypsin (0.25%), testicular hyaluronidase and type I collagenase. The digested material was then resuspended in culture medium (Ham's F12) containing foetal calf serum (10%), glutamine, 4 mM, and penicillin/streptomycin, 100 U.

The cells thus obtained were expanded to the second passage with daily changes of medium. Cell viability was tested by staining with Trypan Blue.

Time Course of Cell Proliferation

To check for any toxicity and/or any possible influence that HYADD™ may have on the chondrocyte proliferation rate, the cells were seeded in the presence of two different concentrations of HYADD™ (0.5 and 1.5 mg/ml of culture medium) for a period of 3 to 9 days. The experiments were performed in triplicate. Cell viability was determined by the MTT method (Dezinot F. et al., J Immunol Methods, 1986, 22(89): 271-277).

Results

The results obtained (FIG. 12) indicate that treatment with HYADD™ at a concentration of 1.5 mg/ml significantly increased the viability of human chondrocytes in all the test preparations as early as the 3$^{rd}$ day of treatment. Moreover, after 9 days of treatment, a significant proliferative effect of the amide derivative could be seen, both for the concentration of 1.5 mg/ml and for the lower one of 0.5 mg/ml.

The results of the study with HYADD™ therefore confirm that said hyaluronic acid derivative has a marked proliferative effect on cultures of human chondrocytes from OA patients.

Considering the results obtained both in vivo and in vitro, it can be said that:

- The amide derivatives of HA called HYADD™ (especially the hexadecyl amide of HA) stimulate proliferation of chondrocytes, the cells responsible for synthesis of the extracellular matrix which, in OA, undergoes a continuous degenerative process associated with chondrocyte death, as previously described in detail;
- The amide derivative, subject of the present invention, has also proved able to stimulate the synthesis of HA by the synoviocytes, thus contributing to normalisation of the turnover of HA (and that of the other glycosaminoglycans) in the synovial fluid, which is otherwise severely impaired in OA joints, as described earlier;
- when tested in vivo, the amide derivative that is subject of the present invention proved able to protect the synovial membrane and joint cartilage from the alterations typical of OA, stabilising the synovia at parameters similar, if not equal, to those of the non-OA control;
- the final viscosity of the treated synovial fluid samples was greater than that observed in OA, and the residence time of the amide derivative in the joint cavity was notably longer than that of other derivatives and/or non-modified HA.

The absolute lack of toxicity of the derivative that is the subject of the present invention, protection from OA degeneration it affords to the cartilage, protection of the synovial membrane and normalisation of the viscosity of the synovial fluid, associated with its considerable residence time in the joint cavity, make this derivative absolutely novel and suitable for use:

- as a new treatment for osteoarthrosis/osteoarthritis,
- as a partial/total substitute for the synovial fluid, in the treatment of joints affected by osteoarthrosis and in cases of inflammation and/or trauma with resulting cartilage and/or synovial damage (associated with pain).

Lastly, we claim its use in the treatment of joints affected by wear due to the physiological aging of the joint structure.

The biomaterial that is the subject of the present invention can be made into various forms (such as gels, hydrogels, powders, microspheres, nanospheres), associated with pharmacologically and/or biologically active substances such as steroids, cytokines, interferone, peptides and nucleic acids, growth factors (such as PDGF, IGF, TGF-β, FGF, GDF5, GDF6) and/or differentiating growth factors (e.g. BMP2 and BMP7), or used as a vehicle for differentiated cells (e.g. chondrocytes, fibroblasts, synoviocytes, osteoblasts/osteocytes), or non-differentiated cells such as mesenchymal cells.

The amide HA derivatives that are the subject of the present invention can be formulated in all the ways known to an expert in the field, in association with stabilisers, excipients, preservatives and/or any other molecule that an expert might think useful, to obtain the best possible pharmaceutical formulation.

For purely descriptive purposes, and without being limited thereby, we report some examples for the preparation of the amide HA derivatives (HYADD™) that are the subject of the present invention:

Example 1

Preparation of the Hexadecylamide of Hyaluronic Acid with a Degree of Amidation of 5%

Two grams (3.2 mM) of tetrabutylammonium salt of HA (HA/TBA) is solubilised in 100 ml of DMSO. The solution is insufflated with HCL vapours or treated with 60 µl of methane sulphonic acid till it reaches a pH value of between 4.5 and 5. Subsequently, 52 grams (0.32 mM) of carbonyl diimidazole was added to the solution, which is shaken at room temperature for 1 hour, then 780 mg (3.2 mM) of hexadecylamine is added. It is left to react for 16-18 hours, after which 5 ml of a saturated NaCl solution is added and the product obtained is precipitated with 200 ml of acetone, filtered and vacuum-dried. The final degree of amidation is performed in HPLC after basic hydrolysis of a small quantity of the product thus obtained.

Example 2

Preparation of the Hexadecylamide of Hyaluronic Acid with a Degree of Amidation of 2%

The procedure is the same as in Example 1, modifying only the quantity of carbonyldiimidazole to be added, in this case 30 mg.

The invention being thus described, it is clear that these methods can be modified in various ways. Such modifications are not to be considered as divergences from the spirit and purpose of the invention, and any modification that would appear evident to an expert in the field comes within the scope of the following claims.

The invention claimed is:

1. A method of treating of joints affected by a condition selected from the group consisting of osteoarthritis, trauma that causes damage to the cartilage and/or synovia, inflammation, and wear due to aging of the joint surfaces and joint cartilage structure comprising administering an effective amount of a hexadecyl amide derivative of hyaluronic acid having a degree of amidation between 0.1% and 5% to an individual in need thereof, and wherein the hexadecyl amide derivative of hyaluronic acid is administered by intraarticular injection.

2. The method of claim 1, wherein said hexadecyl amide derivative of hyaluronic acid is formed by an amide bond between a carboxy group of hyaluronic acid and the amine group of hexadecyl amine.

3. The method according to claim 1 in which the mean degree of amidation is 2%.

4. The method according to claim 1 in which the mean degree of amidation is 5%.

5. The method according to claim 1 in which the hexadecyl amide derivatives are water soluble.

6. The method according to claim 5 in which the molecular weight of the hyaluronic acid ranges between 400 and 3,000,000 Da.

7. The method according to claim 6, wherein said hexadecyl amide derivative is administered in the form of a gel, hydrogel, powder, microsphere, or nanosphere.

8. The method according to claim 1 wherein the administration further comprises bone morphogenetic protein 2 (BMP2) and/or bone morphogenetic protein 7 (BMP7) (differentiating growth factors).

9. The method according to claim 1 wherein said hexadecyl amide derivative is administered in the form of a gel, hydrogel, powder, microsphere, or nanosphere.

10. The method of according to claim 1 wherein the administration of amide derivatives of hyaluronic acid further comprises administering one or more steroids, cytokines, interferons, peptides, nucleic acids, and/or growth factors.

11. The method of treatment according to claim 1 wherein said amide derivatives of hyaluronic acid act as a vehicle for cells.

12. The method of treatment according to claim 11 wherein said amide derivatives of hyaluronic acid stimulate proliferation of chondrocytes and/or mesenchymal cells.

13. A method for treating joints affected by osteoarthritis, osteoarthrosis and/or wear due to aging of the joint structure comprising administering to an individual in need thereof an effective amount of a hexadecyl amide derivative of hyaluronic acid having a degree of amidation of between 0.1% and 5%, and wherein the hexadecyl amide derivative of hyaluronic acid is administered by intraarticular injection.

14. A method of stimulating the proliferation of chondrocytes comprising administering to an individual in need thereof an effective amount of a hexadecyl amide derivative of hyaluronic acid having a degree of amidation of between 0.1% and 5%, wherein the said administration is by intraarticular injection.

15. A method of stimulating the synthesis of hyaluronic acid by synoviocytes from osteoarthritic joints comprising administering to an individual in need thereof an effective amount of a hexadecyl amide derivative of hyaluronic acid having a degree of amidation of between 0.1% and 5%, wherein the said administration is by intraarticular injection.

16. A method of normalizing the viscosity of synovial fluid of osteoarthritic joints comprising administering an effective amount of a hexadecyl amide derivative of hyaluronic acid having a degree of amidation between 0.1% and 5% to an individual in need thereof, and wherein the hexadecyl amide derivative of hyaluronic acid is administered by intraarticular injection.

17. The method according to claim 1, wherein said administration protects the synovial membrane and cartilage from degeneration caused by osteoarthritis.

18. The method according to any one of claims 1 and 13-17, wherein the molecular weight of the hyaluronic acid ranges between 100,000 and 1,000,000 Da.

19. The method according to any one of claims 1 and 13-17, wherein the molecular weight of the hyaluronic acid ranges between 500,000 and 750,000 Da.

20. A method of normalizing the viscosity of the hyaluronic acid (HA) turnover of the synovial fluid of osteoarthritic joints comprising administering an effective amount of a hexadecyl amide derivative of hyaluronic acid having a degree of amidation between 0.1% and 5% to an individual in need thereof, and wherein the hexadecyl amide derivative of hyaluronic acid is administered by intraarticular injection.

21. A method of treating of joints affected by a condition selected from the group consisting of osteoarthritis, trauma that causes damage to the cartilage and/or synovia, inflammation, and wear due to aging of the joint surfaces and joint cartilage structure structure comprising administering an effective amount of a hexadecyl amide derivative of hyaluronic acid having a degree of amidation between 0.1% and 5% to an individual in need thereof, and wherein the hexadecyl amide derivative of hyaluronic acid is administered by intraarticular injection, and wherein said hexadecyl amide derivative exhibits a longer residence time in an osteoarthritic joint as compared to native hyaluronic acid.

22. A method of treating of joints affected by a condition selected from the group consisting of osteoarthritis, trauma that causes damage to the cartilage and/or synovia, inflammation, and wear due to aging of the joint surfaces and joint cartilage structure structure comprising administering an effective amount of a hexadecyl amide derivative of hyaluronic acid having a degree of amidation between 0.1% and 5% to an individual in need thereof, and wherein the hexadecyl amide derivative of hyaluronic acid is administered by intraarticular injection, and wherein said administration reduces the pain associated with osteoarthritis.

23. A method of stimulating the proliferation of chondrocytes consisting of administering to an individual in need thereof an effective amount of a hexadecyl amide derivative of hyaluronic acid having a degree of amidation of between 0.1% and 5%, wherein the said administration is by intraarticular injection.

24. A method for treating joints affected by osteoarthritis, osteoarthrosis and/or wear due to aging of the joint structure comprising intra-articularly administering to an individual in need thereof an effective amount of a hexadecyl amide derivative of hyaluronic acid having a degree of amidation of between 0.1% and 5%, and wherein the hexadecyl amide derivative of hyaluronic acid is administered as a partial and/or total substitute for the synovial fluid.

25. A method for treating joints affected by osteoarthritis, osteoarthrosis and/or wear due to aging of the joint structure comprising administering to the joint cavity of an individual in need thereof an effective amount of a hexadecyl amide derivative of hyaluronic acid having a degree of amidation of between 0.1% and 5%, and wherein the hexadecyl amide derivative of hyaluronic acid is administered by intraarticular injection.

26. The method according to claim 19, wherein said degree of amidation is between 2-3%.

27. The method according to any one of claims 20-22, wherein the molecular weight of the hyaluronic acid ranges between 500,000 and 750,000 Da.

28. The method according to claim 27, wherein said degree of amidation is between 2-3%.

29. The method according to any one of claims 24-25, wherein the molecular weight of the hyaluronic acid ranges between 500,000 and 750,000 Da.

30. The method according to claim 29, wherein said degree of amidation is between 2-3%.

31. The method according to claim 29, wherein said hexadecyl amide derivative is administered in the form of a gel or hydrogel.

32. The method according to claim 30, wherein said hexadecyl amide derivative is administered in the form of a gel or hydrogel.

* * * * *